(12) United States Patent
Hurst (10) Patent No.: US 7,774,979 B2
(45) Date of Patent: Aug. 17, 2010

(54) PROCESS OF PHOTOMORPHOGENICALLY ENHANCING PLANTS

(76) Inventor: William E. Hurst, P.O. Box 20332, Santa Barbara, CA (US) 93105

( * ) Notice: Subject to any disclaimer, the term of this patent is extended or adjusted under 35 U.S.C. 154(b) by 310 days.

(21) Appl. No.: 11/835,491

(22) Filed: Aug. 8, 2007

(65) Prior Publication Data

US 2008/0120736 A1    May 22, 2008

Related U.S. Application Data

(60) Provisional application No. 60/860,057, filed on Nov. 20, 2006.

(51) Int. Cl.
*A01G 13/02* (2006.01)
(52) U.S. Cl. ...................... 47/58.1 LS; 47/29.3; 47/32.3
(58) Field of Classification Search .................... 47/17, 47/29.3, 58.1 LS; 52/204.5
See application file for complete search history.

(56) References Cited

U.S. PATENT DOCUMENTS

| | | | | | |
|---|---|---|---|---|---|
| 5,262,233 | A | * | 11/1993 | Sudo et al. ................... | 428/327 |
| 5,557,171 | A | * | 9/1996 | Marlor et al. ................ | 313/636 |
| 5,610,108 | A | * | 3/1997 | Watzke et al. ................. | 501/59 |
| 5,885,915 | A | * | 3/1999 | Bako et al. .................... | 501/66 |
| 6,118,216 | A | * | 9/2000 | Marlor ......................... | 313/636 |
| 6,284,686 | B1 | * | 9/2001 | Marlor ......................... | 501/64 |
| 7,176,024 | B2 | | 2/2007 | Branson et al. | |
| 7,217,673 | B2 | * | 5/2007 | Naumann et al. .............. | 501/66 |
| 2003/0211014 | A1 | | 11/2003 | Jacquorie et al. | |
| 2004/0132604 | A1 | * | 7/2004 | Grun et al. ..................... | 501/65 |
| 2007/0151149 | A1 | * | 7/2007 | Karpinski .............. | 47/58.1 LS |
| 2007/0289207 | A1 | * | 12/2007 | May et al. ....................... | 47/17 |

FOREIGN PATENT DOCUMENTS

| | | | |
|---|---|---|---|
| EP | 1872652 A1 | * | 1/2008 |
| WO | WO 2006/098285 | * | 9/2006 |
| WO | WO 2007/085842 A1 | | 8/2007 |

OTHER PUBLICATIONS

Dohring, Thorsten et al. "Spectral Shaping of Artificial UV-B Irradiation for Vegetation Street Research" J. Plant Physiol, vol. 148, pp. 115-119 (1996).
Ioannidis, Daphne et al. UV-B is Required for Normal Development of Oil Glands in *Ocimum basilicum* L. (Sweet Basil), Annals of Botany 90: 453-460, 2002.
Bassman, John H. "Ecosystem Consequences of Enhanced Solar Ultraviolet Radiation; Secondary Plant Metabolites as Mediators of Multiple Trophic Interactions in Terrestrial Plant Communities" Photochemistry and Photobiology, 2004, 79(5): 382-398.
Paul, Nigel D. "Ecological roles of solar UV radiation: towards an integrated approach", Trends in Ecology and Evolution, vol. 18, No. 1, Jan. 2003, pp. 48-55.
Krizek, Donald T. "Influence of PAR and UV-A in Determining Plant Sensitivity and Photomorphogenic Responses to UV-B Radiation" Photochemistry and Photobiology, 2004, 79(4): 307-315.
"Stress Under the Sun: Spotlight on Ultraviolet-B Responses" Plant Physiology, Aug. 2003, vol. 132, pp. 1725-1727, www.plantphysiol. org, 2003, American Society of Plant Biologists.
Ballare, Carlos L. "Impacts of solar ultraviolet-B radiation on terrestrial ecosystems of Tierra del Fuego (southern Argentina) An overview of recent progress" 2001 Elsevier Science B.V., Journal of Photochemistry and Photobiology B: Biology 62 (2001) 67-77.
Bjorn, L.O. "Evolution of UV-B Regulation and Protection in Plants" Adv. Space Res. vol. 30, No. 6, pp. 1557-1562, 2002.
Briggs, Winslow R. "Photoreceptors in Plant Photomorphogenesis to Date. Fie Phytochromes, Two Cryptochromes, One Phototropin, and One Superchrome" Plant Physiology, Jan. 2001, vol. 125, pp, 85-88, www.plantphysiol.org, 2001, American Society of Plant Physiologists.
Britz, Steven J. "Photomorphogenesis and Photoassimilation in Soybean and Sorghum Grown under Broad Spectrum or Blue-Deficient Light Sources" Plant Physiol. (1990) 94, 448-454.
Brosche, Mikael "Gene regulation by low level UV-B radiation: identification by DNA array analysis", Photchem. Photobiol. Sci. 2002, 1, 656-664.
Cockell, Charles S. "Lack of UV radiation in Biosphere 2—practical and theoretical effects on plants" Ecological Engineering 16 (2000) 293-299.
Franklin, Keara A. "The signal transducing photoreceptors of plants" Int. J, Dev. Biol, 49: 653-664 (2005).
Gitz, Dennis C. "How do UV Photomorphogenic Responses Confer Water Stress Tolerance", Photochemistry and Photobiology, 2003, 78(6): 529-534.
Grammatikopoulos, R, "Differential effects of enhanced UV-B radiation on reproductive effort in two chemotypes of *Mentha spicata* under field conditions", Functional Plant Biology, Csiro Publishing.
Gregianini, Tatiana S. "The Alkaloid Brachycerine is induced by Ultraviolet Radiation and is a Singlet Oxygen Quencers", Photochemistry and Photobiology, 2003, 78(5): 470-474.
Izaguirre, Miriam M. "Convergent Responses to Stress. Solar Ultraviolet/B Radiation and Manduca extra Herbivory Elicit Overlapping Transcriptional Responses in Field-Grown Plants of *Nicotiana longiflora*" Plant Phsiology, Aug. 2003, vol. 132, pp. 1755-1767, www.plantphysiol.org. 2003, American Society of Plant Biologists.
Jansen, Marcel A.K. "Ultraviolet-B radiation effects on plants: induction of morphogenic responses" Physiologia Plantarum 116: 423-429, 2002.

(Continued)

*Primary Examiner*—Rob Swiatek
*Assistant Examiner*—Kristen C Hayes
(74) *Attorney, Agent, or Firm*—Gifford, Krass, Sprinkle, Anderson & Citkowski, P.C.

(57) ABSTRACT

A process for photomorphogenically enhancing plants is presented wherein a natural or artificial light source emits light through a transmittive material. The material is optionally borosilicate glass with a steep edge situation at or near 280 nm so as to selectively filter out light in the UVC or low UVB regions. The glass allows high transmissibility such that as much as 98% of all light at or above the edge situation passes thorough the material. The percent transmission and edge situation may be defined by glass thickness or by combining multiple types of glass. The light is then contacted with a plant whereby a photomorphogenic response is elicited.

16 Claims, 2 Drawing Sheets

OTHER PUBLICATIONS

Karousou, Regina "Effects of Enhanced UV-B Radiation on Mentha Spicata Essential Oils" Pergamon, Phyochemistry vol. 49, No. 8, pp. 2273-2277, 1998.

Kliebenstein, D.J. "Secondary metabolites and plant/environment interactions: a view through *Arabidopsis thaliana* tinged glasses", Plant, Cell and Environment (2004) 27, 675-684.

Mackerness, Soheila A.H. "Plant responses to ultraviolet-B: 280-320 nm) stress: What are the key regulators?" Plant Growth Regulation 32: 27-39, 2000.

Pilkington "Plant Growth Behind Pilkington Energy Advantage Low-E Glass and Pilkington Solar E Solar Control Low-E Glass".

Raviv, Michael "UV Radiation Effects on Pathogens and Insect Pests of Greenhouse-Grown Crops", Photochemistry and Photobiology, 2004, 79(3): 219-226.

Rozema, Jelte "Depletion of stratospheric ozone over the Antarctic and Arctic: Responses of plants of polar terrestrial ecosystems to enhanced UV-B, an overview" Elsevier, Environmental Pollution 137 (2005) 428-442.

Seckmeyer, Gunther "A new sunlight simulator for ecological research on plants" ScienceDirect.

Stratmann, Johannes "Ultraviolet-B radiation co-opts defense signaling pathways" Trends in Plant Science, vol. 8, No, 11, Nov. 2003.

Teklemariam, Thomas Effects of UVB preconditioning on heat tolerance of cucumber (*Cucumis sativus* L.) Environmental and Experimental Botany 50 (2003) 169-182.

Treutter, D. "Significance of Flavonoids in Plant Resistance and Enhancement of Their Biosynthesis" Unit of Fruit Science, Center of Life Sciences Weihenstephan, Technical University of Munich, Plant Biol. 7 (2005): 581-591.

Waters, Elizabeth R. "Molecular Adaptation and the origin of land plants" Molecular Phylogenetics and Evolution 29 (2003) 456-463.

Description of Glasses Used in Corning Labware, Corning website/ Life Sciences.

Ioannidis, Daphne UV-B Required for Normal Development of Oil Glands in *Ocimum basilicum* L. (Sweet Basil) 2002 Annals of Botany 90: 453-460, 2002.

* cited by examiner

PROCESS OF PHOTOMORPHOGENICALLY ENHANCING PLANTS

CROSS-REFERENCE TO RELATED APPLICATIONS

This application is a non-provisional application that claims priority benefit of U.S. Provisional Application Ser. No. 60/860,057 filed Nov. 20, 2006, the contents of which are hereby incorporated by reference.

FIELD OF THE INVENTION

This invention relates in general to the areas of horticulture using artificial lighting systems to illuminate plants and in particular to using controlled ultraviolet (UV) light exposure in the course of plant growth.

BACKGROUND OF THE INVENTION

The visible light spectrum, known as photosynthetically active radiation (PAR), is of paramount importance in plant growth in that PAR light is responsible for driving photosynthesis. However, the role of ultraviolet radiation (UV) in promoting plant growth and survival is less well understood.

UV light itself is broken down into three spectral regions: the ultraviolet A light (UVA) is of wavelengths of between 320 and 400 nm; ultraviolet B light (UVB) is of wavelengths between 280 and 320 nm; and ultraviolet C light (UVC) is of wavelengths between 180 and 280 nm. The eat is bathed in both UVA and UVB light. However, UVC light is almost entirely filtered out by the earth's atmosphere.

Ultraviolet light in the UVB range is higher energy than UVA and responsible for damage to cells and tissues particularly with exposure to low wavelength UVB light. UVB radiation effects on plants that are attributed to susceptibility to pests, for example, include DNA damage (Britt, A. B., *Trends Plant Sci*, 1999; 4:20-25), modification in gene expression (Savenstrand, H. et al., *Plant Cell Physiol*, 2002; 43:402-10; Brosche M. and Strid A., *Physiol Plant*, 2003; 117:1-10), changes in secondary metabolism (Feucht W. et al., *Vitis*, 1996; 35:113-18; Picman A., et al., *Verticillium albo-atrum Biochem Syst Ecol*, 1995; 23:683-93; Glassgen W. et al., *Planta*, 1998; 204:490-98; Norton, R., *J Agr Food Chem*, 1999; 47:1230-35; Wicklow D., et al., *Mycoscience*, 1998; 39:167-72), and changes in leaf anatomy, i.e. leaf thickness and cuticle thickness (Garcia S., et al., *Phytochemistry*, 1997; 44:415-18; Liakoura, V., et al., *Tree Physiol*, 1999; 19:905-08; Raviv, M., and Antignus, Y., *Photochem Photobiol*, 2004; 79:219-26). Additionally, UVB light causes plants to produce UVB absorbing compounds, such as flavonoids and other phenolics, phenolpropenoids, alkaloids, and terpenoids. These secondary responses are generally independent of photosynthesis and produce photomorphogenic responses in UVB recipient plants.

Early experiments analyzing solar UVB effects demonstrated substantially reduced photosynthesis, plant growth, and crop yield. However, these early experiments were performed under unrealistic spectral balances in that high levels of UV were used. In experiments employing balanced levels of UV radiation, UV-induced partitioning of carbon to production of secondary plant metabolites occurs. Enhanced UVB radiation stimulates production of phenolics and flavonoids that serve a protective role by accumulating in leaf epidermal cells and attenuating UV radiation before encounters of sensitive processes in mesophilic cells. Synthesis of bulk methanol soluble UV absorbing compounds increases by 10% following enhanced UVB radiation.

Glasshouse manufacturers continue to claim that blocking UV radiation shows beneficial effects on reducing plant pathogens and insect pests. However, the presence of UV radiation, including high-energy UVB radiation, is actually beneficial to plant physiology and development. Indeed, when plants are subjected to UV light in addition to PAR many benefits are observed including insect and pathogen resistance and elevated levels of DNA repair capability. The reduced crop yields long thought to be the hallmark of increased ultraviolet light exposure, have recently been demonstrated to be inaccurate. The positive effects of UV radiation are not observed unless full spectrum light is present, including UVA, UVB, and photosynthetically active radiation. However, in radiation controlled studies in which UV and PAR are used simultaneously, high doses of UVB radiation relative to UVA causes some leaf damage in plants suggesting that the more unnatural the spectrum, the greater the damage caused by ultraviolet radiation. (Krizek, 1993; Caldwell, 1994.)

Gene expression is positively regulated by exposure to natural levels of ultraviolet radiation. As many as 70 UVB responsive plant genes have been identified that control mechanisms such as photosynthesis, pathogenesis, and the generation of antioxidants. Several processes regulated by UVB radiation are related to increased or enhanced plant color or fragrance. This modified genetic expression, translation, or modification pattern in the presence of UVB radiation partially explains why clones from the same plant grown in artificial lighting and sunlight look, taste and smell different than their genetic identicals grown in natural sunlight.

A majority of plants show significant benefit from ultraviolet light. Many of these are economically important plants such as herbs, drug producing plants, ornamental flowers, and food crops. Benefits of UV light include increased immune responses, enhanced pigmentation and aroma, and altered plant architecture such as shape, flower number and volume, and thricome density. A meta analysis of numerous plant species suggests that insect damage actually decreases with increasing doses of UVB light. (Bothwel, 1994; Mazza, 1999.) This response has been demonstrated in agricultural as well as in native plants. (Id.; Rousseaux, 1998.) For example, Isaguire, 2003 showed that expression of 20% of insect fighting genes of tobacco are increased after exposure to UVB radiation. These include proteinase inhibitors that inactivate insect digestive tract (Ryan, 1990) and furanocoumarin that results in slower development of insect larvae (McCloud, 1994). Production of insect repelling phenols is also observed following increased solar UVB radiation. (Fuglevand et al., 1996.) Defense to insects includes the formation of flavonoids or pigments that absorb UV in the 220 to 380 nanometer range. (Ormrod, 1995.) It is hypothesized that flavonoids and other chemicals produced in response to UV shield the plant by absorbing light in the UV range, inhibiting insect attachment and further scavenging free radicals.

Supplemental ultraviolet light on tomato plants produces a thickening of the skin that also increases resistance to insects such as boring insects. Other beneficial characteristics are simultaneously present such as the flavor of the pulp is considerably more complex and desirable. Fruit skin toughening is also found in naturally increased UV exposure. In analyses of plants in Tierra del Fuego on the southernmost tip of South America, which is regularly affected by severe ozone depletion increasing the levels of ultraviolet radiation exposure from the sun, insects prefer plant tissue before it is exposed to UVB light. (Ballaré, 2001.) An alternative hypothesis is that insects are refracted by the altered chemical production in leaves exposed to UVB light. In either case, UVB exposure is overall beneficial to plants.

Enhanced pigmentation is seen in many species after exposure to UV light. This is an important observation in that commercially important dyes are produced in plants. (Gilbert and Cooke, 2001.) The synthesis of dyes may be increased by exposure of these plants to UVB or UVA light. Also, enhanced pigmentation of ornamental flowers, especially noted in blue, black and purple tones, is seen after exposure of these plants to UVB light. (Kevan, 2001.) The increase in pigmentation as well as flavonoid production are well documented in response to ultraviolet light. Increase in flavonoid compounds is attributed to the beneficial effects in fruit, vegetables, tea, and red wine grapes to name a few. A specific non-limiting example is the production of anthocyanin that is increased in response to ultraviolet light exposure. The presence of anthocyanin causes roses to appear red to blue depending on the pH in which they are grown. This is seen most often in the leaves of juvenile plants as a reddish hue which disappears as the new leaves mature. However, increased anthocyanin production requires high levels of photosynthetically active radiation alongside increased UV levels. (Steyn, 2002.) As such, a gardener growing roses will see this effect when both UV and photosynthetically active light are present in optimal conditions.

Aromatic oils are also enhanced by in output by ultraviolet light. Such oil output is increased in basil and mint, for example. (Johnson, 1999.) These essential oils are concentrated in glandular thricomes which appear to benefit significantly from UVB radiation.

Auxin levels which absorb UVB light are photo degraded by levels of UVB. However, ethylene which causes radial growth and less elongation in plants is increased after UVB irradiation in sunflower seedlings (Ross and Tevini, 1995) and pear seedlings (Prediери et al., 1993).

UV light exposure increases expression of many of the greater than 25,000 terpenoids known with many with diverse functions in plants. Anti-insecticidal activity is achieved by increased levels of pyrethin which is a natural insecticide (Harbourne, 1991). Beneficial insects may also be attracted by terpenoids such as pollinators and predatory wasps.

Alkaloids are found in 20% of flowering plants are enhanced by UV light. Greater than 12,000 different alkaloids are known in plants and may be economically important as pharmaceuticals including morphine, nicotine, caffeine and cocaine. They are also important as insecticides and other deterrents. Indeed nicotine from tobacco was one of the first insecticides deployed by humans. Phenolic compounds, which illustratively include coumarins, furanocoumarins, and flavonoids, are also produced in the presence of ultraviolet light. There are more than 4,500 flavonoids known. Many flavonoids are strongly colored and used by plants and flowers and fruits to promote pollination and seed dispersal. Thus, UV induced phenolic compounds increases the ornamental desirability of flowering plants or fruits.

Finally, plant shape, architecture, flower number, and thricomes are enhanced or affected by the presence of ultraviolet B radiation. For instance, both UVA and UVB inhibit stem elongation in a wide variety of plants. Decreased elongation is attributed to UV induced destruction of the plant hormone auxin, however increases in the hormone ethylene cause greater radial growth and less elongation, as has been seen in sunflower seedlings and pear seedlings. (Ros and Tevinin, 1995; Prediere, 1993.) These architectural effects may be exploited to improve handling and growing procedures for crops. For example, lower levels of stem elongation can allow for greater stacking capability within a single greenhouse or light irradiated structure increasing crop yield per unit area. Also, balanced light conditions consisting of PAR in addition to UV radiation produce an increase in flower numbers inside a glasshouse. (Grammatikopoulos, 1998; Day, 1999.) Increased diameter of the flowers is also achieved. (Petropoulou, 2001.) In general monocots are more responsive to increased levels of UVB in glasshouses illuminated as in the instant invention than are dicots. (Barnes, P., *Am J Bot*, 1990; 77:1354-60.)

These studies suggest that plants are improved in their yield or ornamental appearance by a proper balance between UV radiation and other light wavelengths. The problem is that high intensity bulbs are limited in the amount of ultraviolet radiation produced to approximately 3% of the total light output. (ANSI C78.38-2005) Therefore, given that UV light is both beneficial to photomorphogenic properties of plants and harmful if used improperly, there is a need for a process of irradiating plants using an artificial light source so as to improve the growth, appearance, disease resistance and desirability of the plants and their fruit.

SUMMARY OF THE INVENTION

A process of illumination plants is described wherein at least one light source is present that emits light in the photosynthetically active region as well as the UVA, UVB, or infrared regions of the spectrum. The light is passed through a light transmittive material and then brought into contact with at least one plant.

The light is sunlight or an artificial light such as a high intensity discharge, fluorescent, metal halide, or high pressure sodium light.

The light transmittive material is made from borosilicate glass, polycarbonate, polyvinyl chloride, polyethylene, polystyrene, fluoropolymers, silicon, nylon, soda lime glass, quartz, cellulose acetate, polyester, or acrylic. This transmittive material is formulated to have an edge situation greater than 280 nm and less than 400 nm. A high degree of transmissibility is maintained in the material with greater than 50% illumination at wavelengths at or above the edge situation with transmissibility greater than 98% preferred. The transmittive material is between 1 and 10 mm thick, preferably between 2 and 5 mm thick.

The plant is altered at least one of many possible photomorphogenic properties illustratively including: defense mechanisms against a pathogen attack, increased levels of UV activating genes, modified gene expression, thickening fruit skin, altering fruit flavor characteristics, increased production of flavonoids, increased fungal resistance, enhancing pigmentation, increased pigment production, essential oil output, resin output, decreased stem elongation, increased radial growth of flowers, altering architectural properties, post harvestability, increases or decreases in flower numbers, increases in thricome density, decreases in leaf area, altering production of terpenoid, alkaloid, phenolpropanoid or other economically valuable compounds such as pharmaceutics.

A structure is created by incorporating the transmittive material into a building such as a glasshouse, greenhouse, or surrounding a light source to form a bulb.

DETAILED DESCRIPTION OF THE PREFERRED EMBODIMENTS

The instant invention has utility in increasing the economic benefit, output and desirability of plants grown in artificial lighting conditions and to benefit such plants. The instant invention is generally related to a container, a glasshouse, or other system for the growing of plants or other crops.

In a preferred embodiment an artificial light source is oriented such that illumination is transmitted through a solid or semi-solid light transmissive material and subsequently contacts plants oriented on the opposite side of the transmissive material as the illumination source. A physical system suitable for use in the instant invention is optionally a wall structure constructed of light transmissive material that allows the passage of light sufficient to promote growth of the biological material stored in a reservoir defined by the wall structure itself. In a preferred embodiment the structure is a glasshouse or other greenhouse type structure. The glasshouse is optionally a small desktop container. It is appreciated that the glasshouse is of any suitable size for the intended use such as large scale crop production in fluid, soil or other solid media, or for a single plant as in a home growing situation. In a preferred embodiment the glasshouse is used for growing ornamental flowers or other home or commercial use plants suitable for a horticulture business.

It is desirable that the transmissibility of the wall material at selected light wavelengths is kept at a maximum. In a preferred embodiment borosilicate glass is used as a transmissive material. Non-limiting examples of glass include borosilicate or flint glass, soda lime glass, and quartz. Preferably the light transmissive material not only allows passage of sunlight but is transparent to promote full passage of all light necessary to support growth including that in the UVB, UVA, photosynthetically active region, and infrared regions. Translucent materials are optionally used to screen out certain wavelengths or light intensities depending on factors and needs of the biological material or the need to reduce accumulation of heat in the structure.

The transmissive material is preferably a borosilicate glass with optical and physical properties including 60% to 70% by weight silicon dioxide, 10% to 15% by weight $B_2O_3$, 5% to 15% by weight $Na_2O$, 5% to 10% by weight $K_2O$, 0.1% to 1% by weight CaO, 0.5% to 3% by weight BaO, 0% to 5% by weight dilithium oxide, 0% to 2% titanium dioxide, 0% to 25% by weight ZnO, and 0% to 0.5% by weight $Sb_2O_3$, and normal refining agents. It is appreciated that the inclusion of oxides of Ti, Zn, or Sb are effective in limiting the amount of UVC transmitted while still passing a limited quantity of UVB needed to promote growth.

Figure 1:
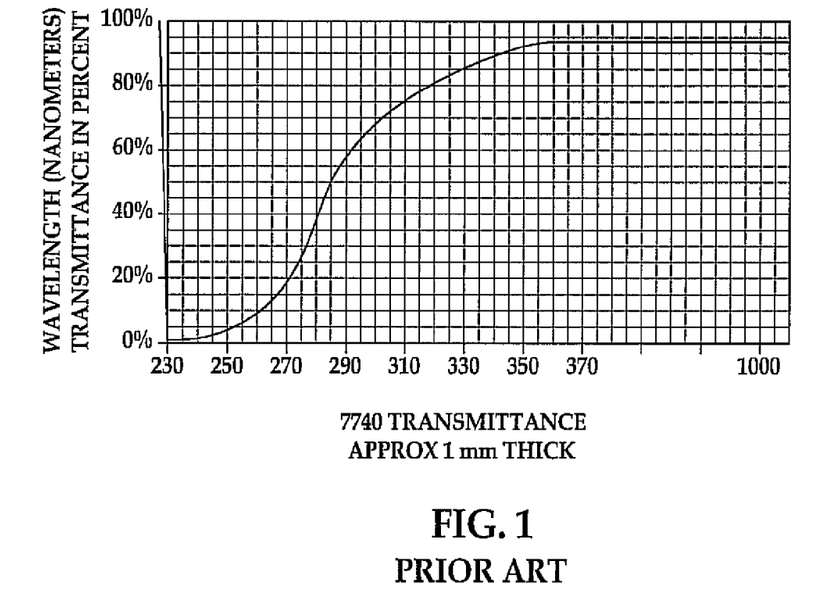
FIG. 1 is a prior art transmittance spectrum for borosilicate glass.

In a preferred embodiment borosilicate glass with a defined edge situation is used as the wall structure. The edge situation or edge wavelength corresponds to half the pure transmission maximum value between the blocking and the permeable range. An illustrative example of an optical borosilicate glass operable in the instant invention is defined in U.S. Patent Application Publication 2004/0132604 A1. The desired spectral characteristics of the borosilicate glass are defined by a steep UV edge in the UV range corresponding to the application purpose, as shown in FIG. 1.

In a preferred embodiment, the light transmissive material has a transmissivity with a point of inflection between 280 and 305 nm and located in the UVB range so as to transmit the UVA and photosynthetically active visible wavelengths while limiting the amount of UVC transmitted to a plant. A point of inflection in the transmission spectrum as used herein is defined as a point where the double derivative spectrum is zero and bounded by non-zero values. The point of inflection is located central to a sigmoid curve of transmissivity as shown for example in FIGS. 1-3 at 285 nm, 307 nm, and 298 nm, respectively. A preferred range for a spectral point of inflection is 285 and 310 nm. This sharp edge situation UVC cutoff achievable by varying the content of titanium dioxide or zinc oxide in the glass system. Borosilicate glass composed simply of normal refining agents contains high levels of transmissibility throughout the IR and visible spectrum with no UVA blockage, little UVB blockage, and total UVC blockage. Thus, doping of the glass with material such as titanium dioxide creates a desired steep edge situation at a desired wavelength.

Preferably the borosilicate glass has a point of inflection between 280 and 320 nm.

Preferably the transmissive material has a steep cutoff at the desired UVB wavelength and the highest possible transmittance of light in the remaining range of the spectrum such as the UVA, visible, and infrared spectral regions. A preferred material has high temporal stability of the spectral transmission characteristics such that temporal transmittance is not altered over the course of time. Optionally, the glass is tempered. Additionally, material suitable in the instant invention optionally has high mechanical stability such that it can define a wall and can resist weathering conditions and the weight of material such as snow or resist damage from projectiles. Finally a material suitable in the instant invention is optionally available in large sheets such that construction of large glasshouses is easily obtainable. It is appreciated that large continuous films, liquid sprays or other treatments, are similarly suitable in the instant invention. Transmissive filtering materials are preferably able to withstand high intensity UVB radiation.

Borosilicate glass thickness used in a preferred embodiment optionally regulates the level of transmittance. In a non-limiting example the thinner the glass material the more light is transmitted. Preferably the glass material allows transmission of greater than 50% of light with a wavelength at or above the edge situation. More preferably light transmission at or above the edge situation is between 90 and 95%. Most preferably the light transmission levels are greater than 95% at or above the edge situation with an optimal level of 98% or greater light transmission at or above the edge situation.

Glass materials as thin as 1 to 2 mm thick are the most beneficial in providing light transmissibility. A 1 mm thick borosilicate glass will block all UVB from a 1 watt lamp and virtually none from a 1000 watt lamp. Thus, the glass thickness is preferably chosen with relation to the intensity of the chosen light source. Preferably the borosilicate glass used is between 1 and 10 mm thick, more preferably between 2 and 5 mm thick. It is appreciated that glass with thickness parameters outside these preferred ranges is optionally employed in the instant invention.

Optionally multiple glass types, compositions, and thicknesses are combined in a single wall situation. For example, glass with greater thickness is optionally employed in regions of high light availability or where the structural integrity of the glasshouse is of paramount concern such as in geographic regions that receive large amounts of snow. Glasshouses suitable for use in the instant invention optionally contain thicker glass on some portions of the ceiling panel and thinner glass structures on other portions of the ceiling or wall. Illumination is optionally adjusted such that higher UV emitting lights are used on wall portions with thicker glass and lower energy UV light emitting bulbs are used where thinner of the glass is used. Optionally the glass panel is movable to rotate or otherwise alter position with adjusting solar light source position.

In maximizing the strength of the structure and simultaneously reducing the amount of energy used, numerous illuminating sources are optionally employed in the instant invention such as sunlight or artificial sources. Artificial light sources optionally include high intensity discharge (HID) lights selected to emit visible light, ultraviolet radiation, or infrared radiation. Preferably, maximum UV radiation emitted from HID lamps is preserved by the chosen glass material. Fluorescent bulbs are optionally employed to selectively emit various wavelengths of ultraviolet radiation such as UVB-313 fluorescent lamps, as well as metal halide (MH) lamps or high pressure sodium (HPS) bulbs. Bulbs optionally employed include MH bulbs suitable for emitting wavelengths between 400 and 500 nm and used for increasing vegetative growth or HPS bulbs suitable for emission of longer wavelengths such as between 500 and 700 nm which are used for voluminous flower production. Lamps are optionally used individually or in combination to provide or supplement ultraviolet light. In a preferred embodiment the light transmissive material totally surrounds the lamp structure such that each lamp structure individually comprises an illuminating unit. More preferably the light source is oriented above or to the side of the biological material. Numerous illuminating units or illuminating sources are optionally employed depending on the required light intensity or spectral characteristics of the light to be illuminated on the biological material. Different light sources are optionally employed at different locations around the biological material. In a non-limiting example, the light sources are more UV emitting above the plant with less UV emitting light sources to the side of the plants to mimic the movement of the sun. Optionally, the light sources are varied at different locations in the glasshouse. In a non-limiting example, more intense UV emitting lights are optionally placed overhead whereas lower emitting light sources are placed lower to the horizon. Each of these light sources are optionally illuminated at different times to mimic movement of the sun.

The inventive process optionally alters stress responses or photomorphogenic properties of the biological material. The photomorphogenic properties altered by the chosen light spectrum are optionally defense mechanisms against a pathogen attack, increased levels of UV activating genes, modified gene expression, thickening fruit skin, altering fruit flavor characteristics, increased production of flavonoids, increased fungal resistance, enhancing pigmentation, increased pigment production, essential oil output, resin output, decreased stem elongation, increased radial growth of flowers, altering architectural properties, post harvestability, increases or decreases in flower numbers, increases in thricome density, decreases in leaf area, altering production of terpenoid, alkaloid, phenolpropanoid or other economically valuable compounds such as pharmaceutics.

Secondary metabolites produced by the altered photomorphogenic characteristics in the instant invention optionally include products such as dyes, polymers, fibers, glues, oils, waxes, flavors, perfumes, and drugs.

The present invention is further illustrated with respect to the following non-limiting examples.

Example 1

Low expansion borosilicate glass suitable in the instant invention is commercially available (Pyrex 7740 borosilicate glass, Corning, Inc.). This glass has the spectral profile as shown in FIG. 1. This glass is manufactured in sheets with a low coefficient of expansion providing mechanical stability. This material is suitable for manufacture into sheets for glasshouse or other biological material growth.

Figure 2:
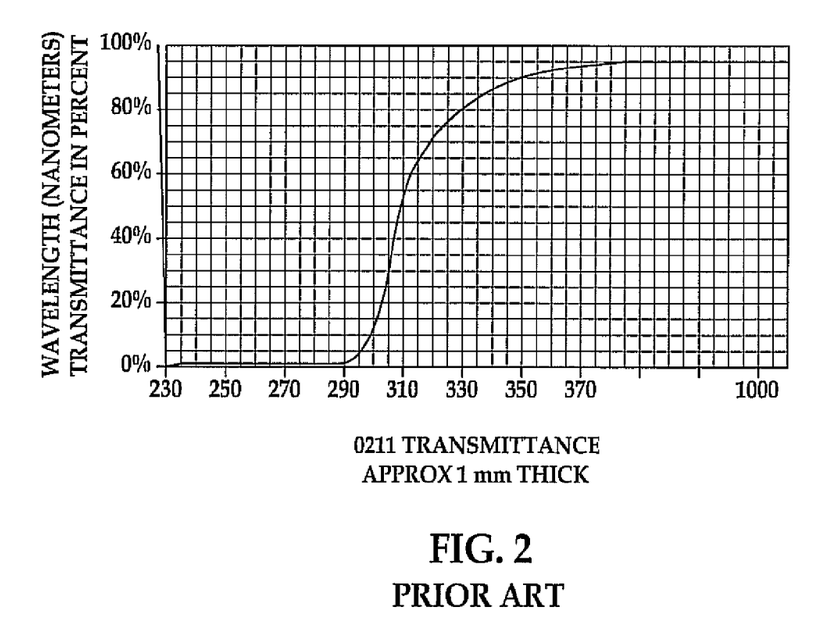
FIG. 2 is a prior art transmittance spectrum for zinc titania glass.
Figure 3:
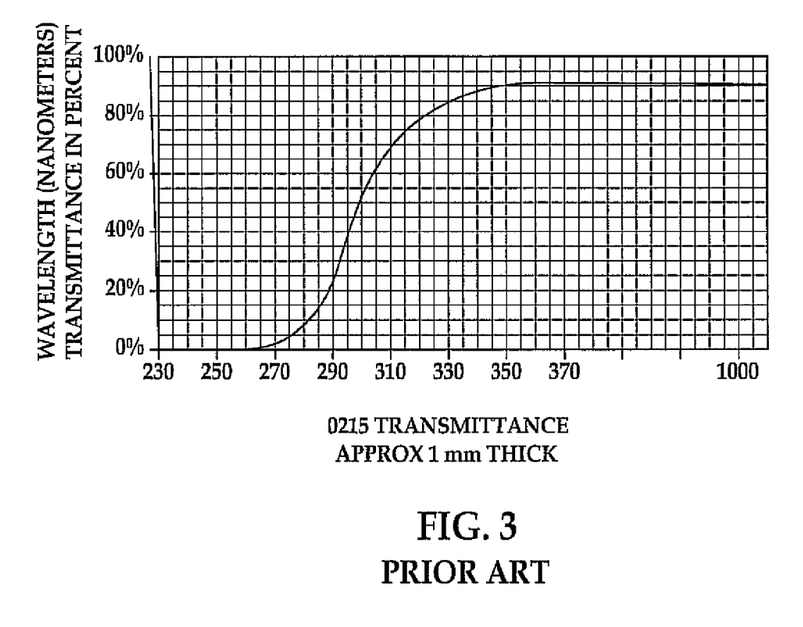
FIG. 3 is a prior art transmittance spectrum for soda lime glass.

Another material suitable in the instant invention is zinc titania glass (Corning, Inc.). The transmission profile of this glass is shown in FIG. 2. This glass is manufactured in small sheets at 1 mm thickness. This glass or other suitable glasses are optionally stabilized by a transparent or metal mesh to provide mechanical stability to the glass while maintaining the desired optical transmission and full light pass characteristics desired. In this fashion large sheets are produced that can be installed on a glasshouse. Alternatively, zinc titania or other glass is used in combination with soda lime glass commonly used for plate glass building purposes. A typical spectral profile of soda lime glass from Corning, Inc. is shown in FIG. 3.

A transmissive material with soda lime glass placed on top of a borosilicate glass will protect the borosilicate glass from solarization increasing the useful life of the transmissive material. (Dohring, T, 1996.)

Example 2

Borosilicate glass (Pyrex 7740) panes of 2 mm thickness used as high transmissibility, steep edge situation filters are placed in an aluminum frame. A combination array of different ent lamps including metal halide, quartz-halogen, blue fluorescent, and UV-B fluorescent lamps to provide the UVB portion of the spectrum (Seckmeyer, G., and Payer, H., *J Photochem Photobiol*, 1993; 21:175-81) are positioned opposite the inventive glass panes from soil containing a mixture of Levington Compost B2 and perliet (3:2). *Ocimum basilicum* L. is grown in the soil and exposed to illuminating conditions for 14 hours per day and cycled through darkness for the remaining 10 hours per day against a like control receiving no UV irradiation. After growth for 15 days, leaves are analyzed for anatomical characterization and quantitation of essential oil from developing and mature leaves as described by Ioannidis et al., 2002. UVB treatment leads to photomorphogenically increased essential oil production in the leaves of both developing and mature plants, with a greater increase in the developing leaves. Leaf gland numbers are not increased. However, increases in oil gland volume are increased and are 35% greater in mature leaves and 20% greater in developing leaves. Importantly, the fragrance of the leaves is pleasantly increased. This increase in fragrance is attributable to increases in the number of broken oil sacks in these plants where the rate of breakage is around 40-45%.

Example 3

Soybeans are grown from seed under light as in Example 2 at 15 kJ/m$^2$/day UVB radiation and in standard greenhouse environmental conditions of temperature and humidity against a like UV irradiation free control. These photomorphogenic soybeans require much lower soil moisture levels as the root structure is enhanced under these growth conditions relative to controls. The photomorphogenic root to shoot ratio is significantly improved providing greater soil penetration and plant-soil interaction which in turn requires reduced water input to maintain growth parameters. These photomorphogenic plants also show increased dry weight mainly attributable to increase root mass. Further, the photomorphogenic relative leaf area ratio decreases in these plants. The lower leaf area is responsible for limiting transpiration loss. However, the photosynthetic quantum efficiency, phytochrome photostationary state, and phytochrome cycling rate remain unchanged in soybeans grown under the inventive conditions. Finally, stomatal density is reduced further leading to increased water use efficiency. Thus, growing soybeans under the inventive conditions produces plants that possess improved water retention, reduced irrigation requirements and also have similar photosynthetic capacity as plants grown otherwise indicating a greatly improved overall growth profile.

Example 4

Wild mint (*Mentha spicata*) is grown in soil in a glasshouse constructed of borosilicate glass made from 69.98% (by weight) $SiO_2$, 11.19% $B_2O_3$, 9.49% $Na_2O$, 7.29% $K_2O$, 0.2% CaO, 1.35% BaO, 0.2% $TiO_2$, 0.3% $Sb_2O_3$, and expected refining agents as described. US 2004/0132604 A1. Illumination is as in Example 1. No changes are observed in photosynthetic capacity, total stem length, chlorophyll content, or photochemical efficiency of photosystem II. However, leaf mass is increased although no change in leaf area is observed. Importantly, seed yield is improved with yields as much as 100% higher. The increased seed production drastically improves replanting procedures and field success.

Example 5

The perennial herb *Silene vulgaris* was analyzed in a glasshouse under light conditions as in Example 1 using glass with light transmission down to 290 nm. Light intensity is 16.2 kJ/m² UVB radiation levels with full UVA and PAR light illumination. Illumination is maintained for 51 days. These herbs produce much higher numbers of seed producing flowers than plants grown in traditional glasshouse lighting conditions. Further, the number of infertile flowers is decreased using the inventive grow lighting process. The seeds produced from the plants grown in the inventive conditions show unchanged germination rates.

Example 6

*Salvia splendens* is grown under conditions of Example 1. These plants demonstrate a more compact stature and improved resistance to handling. These properties greatly improve cultivation and storage capacity improving transport capacity.

References cited herein are indicative of the level of skill in the art to which the invention pertains. These references are hereby incorporated by reference to the same extent as if each individual reference was explicitly and individually incorporated herein.

REFERENCE LIST

1. Allen, D. J., Nogues, S., Baker, N. R. (1998) Ozone depletion and increased UV-B radiation: is there a threat to photosynthesis. *J Exp Bot* 49: 1775-1788.
2. Antignus, Y. (2000) Manipulation of wavelength dependent behaviour of insects: an IPM tool to impede insects and restrict behaviour of insect-borne viruses. *Virus Res.* 71, 213-220.
3. Bacci, L. et al. (1999) UV-B radiation causes early ripening and reduction in size of fruits in two lines of tomato (*Lycopersicon esculentum* Mill.). *Glob. Change Biol.* 5, 635-646.
4. Ballaré(b), C. L., Scopel, A. L., Stapleton, A. E. and Yanovsky, M. J. 1996. Solar ultraviolet-B radiation affects seedling emergence, DNA integrity, plant morphology, growth rate, and attractiveness to herbivore insects in *Datura ferox*. *Plant Physiology* 112:161-170.
5. Ballaré, C. L.; Rousseauxa, M. C.; Searles, P. S.; Zaller, J. G.; Giordano, C. V.; Robson, T. M.; Caldwell, M. M.; Sala, O. E.; Scopel, A. L. Impacts of solar ultraviolet-B radiation on terrestrial ecosystems of Tierra del Fuego (southern Argentina) An overview of recent progress. *Journal of Photochemistry and Photobiology B: Biology* 62 (2001) 67-77.
6. Barnes, P. W., Flint, S. D., Caldwell, M. M. (1990) Morphological responses of crop and weed species of different growth forms to ultraviolet-B radiation. *Am J Bot* 77: 1354-1360.
7. Barnes, J., K. Percy, N. Paul, P. Jones, C. McLaughlin, P. Mullineaux, G, Creissen and A. Wellburn (1996) The influence of UV-B radiation on the physicochemical nature of tobacco (*Nicotiana tabacum* L.) leaf surface. *J. Exp. Bot.* 47, 99-109.
8. Bassman, J. H. Ecosystem Consequences of Enhanced Solar Ultraviolet Radiation: Secondary Plant Metabolites as Mediators of Multiple Trophic Interactions in Terrestrial Plant Communities. *Photochemistry and Photobiology*, 2004, 79(5): 382-398.
9. Bender, K., Blattner, C., Knebel, A., Lordanov, M., Herrlich, P. and Rahmsdorf, H. J. 1997. UV-induced signal transduction. *Journal of Photochemistry and Photobiology B* 37:1-17.
10. Bottwell, M. L., Sherbot, D. M. J., Pollock, C. M. (1994) Ecosystem responses to solar ultraviolet-B radiation: influence of trophic-level interactions, *Science* 265: 97-100.
11. Björn, L. O., Callaghan, T. V., Johnsen, I., Lee, J. A., Manetas, Y., Paul, N. D., Sonesson, M., Wellburn, A. R., Coop, D., Heide-Jorgensen, H. S., Gehrke, C., Gwynn-Jones, D., Johanson, U., Kyparissis, A., Levizou, E., Nikolopoulos, D., Petropoulou, Y., Stephanou, M. (1997) The effects of UV-B radiation on European heathland. *Plant Ecol* 128: 252-264.
12. Björn, L. O., Widell, S., Wang, T., Evolution of UV-B Regulation and Protection in Plants. *Adv. Space Res. Vol.* 30, No. 6, pp. 1557-1562, 2002.
13. Brosché a, M.; Stridb, A. Molecular events following perception of ultraviolet-B radiation by plants. *Physiologia Plantarum*, 117: 1-10. 2003.
14. Brosché , M. et al. (2002) Gene regulation by low level UV-B radiation: identification by DNA array analysis. *Photochem. Photobiol. Sci.* 1, 656-664.
15. Burkhardt, D. (1982) Birds, berries and UV: a note on some consequences of UV vision in birds. *Naturwissenschaften* 69, 153-157.
16. Briggs, W. R.; Olney, M. A. Photoreceptors in Plant Photomorphogenesis to Date. Five Phytochromes, Two Cryptochromes, One Phototropin, and One Superchrome. *Plant Physiol.* 2001; 125(1):85-8.
17. Britt, A. B. (1999) Molecular genetics of DNA repair in higher plants. *Trends Plant Sci* 4: 20-25.
18. Caldwell, M. M.; Flint, S. D.; Searles, P. S.; (1994) Spectral balance and UV-B sensitivity of soybean: a field experiment. *Plant Cell Environ.* 17, 267-276.
19. Caldwell, M. M. et al. (2003) Terrestrial ecosystems, increased solar ultraviolet radiation and interactions with other climatic change factors. *Photochem. Photobiol. Sci.* 1, 29-38.

20. Caldwell, M. M., Flint, S. D. (1997) Uses of biological weighting functions and the need of scaling for the ozone reduction problem. *Plant Ecol* 128: 66-76.
21. Caasi-Lit, M., M. I. Whitecross, M. Nayudu and G. J. Tanner (1997) UV-B irradiation induces differential leaf damage, ultrastructural changes and accumulation of specific phenolic compounds in rice cultivars. *Aust. J. Plant Physiol* 24, 261-274.
22. Child, R., and Smith H., (1987). Phytochrome action in light-grown mustard: Kinetics, fluence-rate compensation and ecological significance. *Planta* 172: 219-229.
23. Chory, J. and Wu, D. Weaving the Complex Web of Signal Transduction. *Plant Physiol.* 2001; 125(1):77-80.
24. Cockell, C. S.; Southern, A.; Herrera, A. Lack of UV radiation in Biosphere 2—practical and theoretical effects on plants. *Ecological Engineering* 16 (2000) 293-299.
25. Conconi, A. et al. (1996) The octadecanoid signaling pathway in plants mediates a response to ultraviolet radiation. *Nature* 383, 826-829.
26. Cooley, N. M., H. M. F. Truscott, M. G. Holmes and T. H. Attridge (2000) Outdoor ultraviolet polychromatic action spectra for growth responses of *Bellis perennis* and *Cynosurus cristatus. J. Photochem. Photobiol. B: Biol.* 59, 64-71.
27. Costa, H. S. and Robb, K. L. (1999) Effects of ultraviolet-absorbing greenhouse plastic films on flight behavior of *Bemisia argentifolii* (*Homoptera: Aleyrodidae*) and *Frankliniella occidentalis* (*Thysanoptera: Thripidae*). *J. Econ. Entomol.* 92, 557-562.
28. Croteau, R., T. M. Kutchan and N. G. Lewis (2000) *Natural products (secondary metabolites)*. In Biochemistry & Molecular Biology of Plants (Edited by B. Buchanan, W. Gruissem and R. Jones), pp. 1250-1318. American Society of Plant Physiologists, Rockville, Md.
29. Day, T. A., Ruhland, C. T., Grobe, C. W., Xiong, F. (1999) Growth and reproduction of Antarctic vascular plants in response to warning and UV radiation reductions in the field. *Oecologia* 119: 24-35.
30. Davies, P. J. (1995) Plant Hormones. Kluwer Academic Publishers, Dordrecht, The Netherlands.
31. Döehring, Thorsten; Koefferlein, Matthias; Thiel, Stephan, and Seidlitz, Harald K. Spectral Shaping of Artificial UV-B Irradiation for Vegetation Stress Research. *Journal of Plant Physiology.* 1996; 148(1/2):115-119.
32. Elena Monte, José M. Alonso, Joseph R. Ecker, Yuelin Zhang, Xin Li, Jeff Young, Sandra Austin-Phillips, and Peter H. Quail, Isolation and Characterization of phyC Mutants in *Arabidopsis* Reveals Complex Crosstalk between Phytochrome Signaling Pathways. *Plant Cell.* 2003 Sep.; 15(9): 1962-1980.
33. Ensminger, P. A. (1993) Control of development in plants and fungi by far-UV radiation. *Physiol. Plant.* 88, 501-508.
34. Fiscus, E. L., Booker, F. L. (1995) Is increased UV-B a threat to crop photosynthesis and productivity? *Photosynth Res* 43: 81-92.
35. Franklin, K. A.; Lamer, V. S., and Whitelam, G. C. The signal transducing photoreceptors of plants. *Int J Dev Biol.* 2005; 49(5-6):653-64.
36. Fuglevand, G., Jackson, J. A., Jenkins, G. I., 1996. UV-B, UV-A and blue light signal transduction pathways interact synergistically to regulate chalcone synthase gene expression in *Arabidopsis. Plant Cell* 8, 2347-2357.
37. Gatehouse, J. A. (2002) Plant resistance towards insect herbivores: a dynamic interaction. *New Phytol* 156: 145-169.
38. Giannini A., Pardossi A., Lercari, B., (1996) The use of UV radiation to control the architecture of *Salvia splendens* plants. I. Effects on plant growth, water relations and gas exchange. *Photochem Photobiol* 64: 123-130.
39. Gitz, D. C.; Liu-Gitz, L. How do UV Photomorphogenic Responses Confer Water Stress Tolerance? *Photochemistry and Photobiology,* 2003, 78(6): 529-534.
40. Gilbert, K. G. and Cooke, D. T. (2001) Dyes from plants: past usage, present understanding and potential. *Plant Growth Reg.* 34, 57-69.
41. Grammatikopoulos G., Karousou R., Kokkini S., Manetas Y. (1998). Differential effects of UV-B radiation on reproductive effort in two chemotypes of *Mentha spicata* under field conditions. *Austr J Plant Phys* 25: 345-351.
42. Gregianini, T. S.; da Silveira, V. C.; Porto, D. D.; Kerber, V. A.; Henriques, A. T., and Fett-Neto, A. G. The alkaloid brachycerine is induced by ultraviolet radiation and is a singlet oxygen quencher. *Photochem. Photobiol.* 2003 November; 78(5):470-4.
43. Gunasekera, T. S., Paul, N. D. and Ayres, P. G. 1997. The effects of ultraviolet-B (UV-B: 290-320 nm) radiation on blister blight disease of tea (*Camellia sinensis*). *Plant Pathology* 46:179-185.
44. Halliday, K. J., Koorneef M., Whitelam G. C., (1994). Phytochrome B and at least one other phytochrome mediate the accelerated flowering response of *Arabidopsis thaliana* L. to low red/far-red ratio. *Plant Phlysiol.* 104: 1311-1315.
45. Hajnos, M. K. et al. (2001) The influence of ultraviolet radiation on the content of pharmacologically active taxoids in yew tissues. *Phytomedicine* 8, 139-143.
46. Harbourne, J. B. (1991) *Flavonoid pigments*. In Herbivores: Their Interactions with Secondary Metabolites, 2nd ed. (Edited by G. A. Rosenthal and M. R. Berenbaum), pp. 389-430. Academic Press, San Diego.
47. Hatcher, P. E. and Paul, N. D. 1994. The effect of elevated UV-B radiation on herbivory of pea by Autographa gamma. *Entomologia Experimentalis et Applicata* 71:227-233.
48. Hillig, K. W., Mahlberg, P. G., A Chemotaxonmic, 2004, Analysis of Cannabinoid Variation in Cannabis (*Cannaebceae*), *American Journal of Botany* 91(6): 966-975.
49. Huang, S., Dai, Q., Peng, S., Chavez, A. Q., Miranda, M. L. L., Visperas, R. M. and Vergara, B. S. 1997. Influence of supplemental ultraviolet-B on indoleacetic acid and calmodulin in the leaves of rice (*Oryza sativa* L.). *Plant Growth Regulation* 21:59-64.
50. Izaguirre, M. M.; Scopel, A. L.; Baldwin, I. T.; Ballare, C. L. Convergent Responses to Stress. Solar Ultraviolet-B Radiation and *Manduca sexta* Herbivory Elicit Overlapping Transcriptional Responses in Field-Grown Plants of *Nicotiana longiflora. Plant Physiology,* August 2003, Vol. 132, pp. 1755-1767.
51. Jansen, M. A. K., 2002, Ultraviolet-B radiation effects on plants: induction of morphogenic responses. *Physiologia Plantarum:* 116: 423-429.
52. Jenkins, G. I., Fuglevand, G. and Christie, J. M. 1997. *UV-B perception and signal transduction*. In Plants and UV-B: Responses to Environmental Change, P. Lumsden (ed.), Cambridge Univ. Press, UK, pp. 135-156.
53. Johnston, H. S. 1971. Reduction of stratospheric ozone by nitrogen oxide catalysts from supersonic transport exhaust. *Science* 173:517-522.
54. Johnson, C. B. et al. (1999) Substantial UV-B-mediated induction of essential oils in sweet basil (*Ocimum basilicum* L.). *Phytochemistry* 51, 507-510.
55. Jordan, B. R., 1996. The effects of ultraviolet-B radiation on plants: A molecular perspective. *Advances in Botanical Research* 22:97-162.

56. Jordan, B. R., Chow, H. J., Anderson, J. M. (1992) Changes in mRNA levels and polypeptide subunits of ribulose 1:5-bisphosphate carboxylase in response to supplementary ultraviolet-B radiation. *Plant Cell Environ* 15: 91-98.
57. Karabourniotis, G., K. Papadopoulos, M. Papamarkou and Y. Manetas (1992) Ultraviolet-B radiation absorbing capacity of leaf hairs. Physiol. *Plant* 86, 414-418.
58. Karousou, R., Grammatikopoulos, G., Lanaras, T., Manetas, Y., Kokkini, S. 1998. Effects of enhanced UV-B radiation on Mentha spicata essential oil. *Phytochemistry* 49: 2273-2277.

The foregoing description is illustrative of particular embodiments of the invention, but is not meant to be a limitation upon the practice thereof. The following claims, including all equivalents thereof, are intended to define the scope of the invention.

The invention claimed is:

1. A process of radiating a plant with limited spectrum ultraviolet light to induce photomorphogenic growth comprising:
   illuminating a light source to produce light with wavelengths extending between ultraviolet C (UVC) and infrared spectral regions;
   maximizing ultraviolet B exposure and minimizing UVC exposure to light from said light source by transmitting the light from said light source through a single sheet of borosilicate glass having a thickness of between 1 and 10 millimeters, said single sheet of borosilicate glass being non-transmissive of at least 95% of the UVC and more permissive of remaining spectral regions, wherein said borosilicate glass has a point of inflection wavelength between 280 nanometers and 320 nanometers; and
   exposing the plant to transmitted light to induce a photomorphogenic response induced by UVB exposure.

2. The process of claim 1 wherein said light source is sunlight or artificial light.

3. The process of claim 2 wherein said light source is artificial light selected from the group comprising: high intensity discharge, fluorescent, metal halide, and high pressure sodium.

4. The process of claim 1 wherein said single sheet of borosilicate glass is doped with a metal oxide of an element selected from the group consisting of Li, Ti, Zn, Sb, and combinations thereof.

5. The process of claim 4 wherein said metal oxide is present between 0.1 and 10 total weight percent.

6. The process of claim 4 wherein said metal oxide comprises 0% to 5% by weight dilithium oxide, 0% to 2% titanium dioxide, 0% to 25% by weight ZnO, and 0% to 0.5% by weight $Sb_2O_3$, or combinations thereof present to at least 0.1% by weight.

7. The process of claim 4 wherein said borosilicate glass comprises between 0.1 and 10 total weight percent of a said metal oxide.

8. The process of claim 4 wherein said metal oxide is combination $TiO_2$ and $Sb_2O_3$ and said glass transmits greater than 50% of the light with a wavelength longer than the point of inflection wavelength.

9. The process of claim 1 further comprising at least one light transmittive glass wherein said light transmittive glass and said single sheet of borosilicate glass in combination transmit greater than 95% of all the light with wavelengths longer than the point of inflection wavelength.

10. The process of claim 9 wherein said light transmittive glass is greater than or equal to 1 millimeter thick.

11. The process of claim 9 wherein said light transmittive glass is between 1 millimeter and 10 millimeters thick.

12. The process of claim 9 wherein light transmittive glass is between 2 millimeters and 5 millimeters thick.

13. The process of claim 1 further comprising altering the photomorphogenic properties of said plant.

14. The process of claim 13 wherein said photomorphogenic property is selected from the group consisting of: defense mechanisms against a pathogen attack, increased levels of UV activating genes, modified gene expression, thickening fruit skin, altering fruit flavor characteristics, increased production of flavonoids, increased fungal resistance, enhancing pigmentation, increased pigment production, essential oil output, resin output, decreased stem elongation, increased radial growth of flowers, altering architectural properties, post harvestability, increases or decreases in flower numbers, increases in thricome density, decreases in leaf area, altering production of terpenoid, alkaloid, phenolpropanoid or other economically valuable compounds such as pharmaceutics.

15. The process of claim 1 wherein said single sheet of borosilicate glass forms a ceiling panel of a greenhouse.

16. The process of claim 1 wherein said single sheet of borosilicate glass and said light source combine to form a bulb.

* * * * *